United States Patent
Lariviere et al.

(10) Patent No.: US 6,515,195 B1
(45) Date of Patent: Feb. 4, 2003

(54) SANITARY NAPKIN WITH IMPROVED LIQUID RETENTION CAPABILITY

(75) Inventors: Christiane Lariviere, Montreal (CA); Roya Mohmad, Montreal (CA); Sylvain Mongeau, Mascouche (CA); Zulfikar Murji, Verdun (CA); Vu Hien Nguyen, East Windsor, NJ (US); Leonard G. Rosenfeld, East Windsor, NJ (US)

(73) Assignee: Johnson & Johnson Inc., Montreal (CA)

( * ) Notice: Subject to any disclaimer, the term of this patent is extended or adjusted under 35 U.S.C. 154(b) by 0 days.

(21) Appl. No.: 09/477,313

(22) Filed: Jan. 4, 2000

Related U.S. Application Data

(63) Continuation-in-part of application No. 09/374,514, filed on Aug. 16, 1999, now abandoned.

(51) Int. Cl.$^7$ ................................................ A61F 13/15
(52) U.S. Cl. ................. 604/380; 604/383; 604/385.101
(58) Field of Search ............................... 604/367, 370, 604/371, 372, 374, 375, 378–380, 385.01, 385.03–385.05, 385.101, 386, 387, 389, 383

(56) References Cited

U.S. PATENT DOCUMENTS

| | | | |
|---|---|---|---|
| 4,610,678 A | | 9/1986 | Weisman et al. |
| 4,795,455 A | * | 1/1989 | Luceri et al. ............... 604/386 |
| 5,267,992 A | * | 12/1993 | Van Tilburg ................ 604/387 |
| 5,466,513 A | * | 11/1995 | Wanek et al. ............... 428/218 |
| 5,514,104 A | * | 5/1996 | Cole et al. .................. 604/366 |
| 5,830,555 A | * | 5/1996 | Sirinivasan ................. 428/137 |
| 5,562,645 A | | 10/1996 | Tanzer et al. |
| 5,575,786 A | | 11/1996 | Osborn, III |
| 6,007,528 A | * | 12/1996 | Osborn, III ................. 604/387 |
| 5,609,588 A | * | 3/1997 | DiPalma et al. ............ 604/369 |

FOREIGN PATENT DOCUMENTS

EP           0 781 537 A1      7/1997

\* cited by examiner

*Primary Examiner*—Aaron J. Lewis
*Assistant Examiner*—Jamisue Webb
(74) *Attorney, Agent, or Firm*—James P. Barr

(57) ABSTRACT

The invention provides a sanitary absorbent article, such as a feminine protection device, having a fibrous, liquid permeable body-facing cover layer, and an absorbent system, which exhibits particular rewet characteristics when subjected to mechanical stress. The sanitary absorbent article has a thickness of less than or equal to 5 mm, a capacity of at least 18 grams, a rewet potential of less than or equal to 0.8 grams, and a flexural resistance of less than 700 g.

38 Claims, 4 Drawing Sheets

SANITARY NAPKIN WITH IMPROVED LIQUID RETENTION CAPABILITY

This is a continuation-in-part of application Ser. No. 09/374,514, filed Aug. 16, 1999, now abandoned.

FIELD OF THE INVENTION

The present invention relates generally to sanitary absorbent articles and in particular to such articles, for example sanitary napkins which are thin, yet highly absorbent.

BACKGROUND OF THE INVENTION

Sanitary absorbent articles find wide and varied use in absorbing and trapping body fluids and maintaining body surfaces in a state of dryness and comfort. The development of materials having a high liquid absorption capacity per unit volume has allowed the required overall thickness of sanitary absorbent articles to be reduced providing products which are more comfortable and less obtrusive to wear. Such articles find use, for example in feminine protection devices such as sanitary absorbent napkins. Thin sanitary napkins are generally constructed of multiple layers of material each having a particular function, as for example disclosed in U.S. Pat. No. 5,575,786 to T. W. Osborne III. The sanitary napkin disclosed in this document includes a top sheet which is placed nearest the body surface of the wearer, a first absorbent layer which may function as an acquisition or transfer sheet with a relatively open structure having a relatively high void volume for accepting fluid and transporting fluid to a second absorbent layer which serves as the main dispository for liquid absorbed by the napkin. The napkin also has a barrier sheet which is impervious to liquid absorbed into the second absorbent layer and serves as a protective barrier between the second absorbent layer material and the wearers clothing. The second absorbent layer has a high liquid absorption capacity relative to the top and first absorbent layers and can be made from materials such as wood pulp, creped cellulose wadding, absorbent foams and sponges, polymeric fibres and polymeric gelling agents. The average thickness of the napkin disclosed in U.S. Pat. No. 5,575,786 is less than 2.6 mm.

A problem which confronts designers of sanitary absorbent napkins is their ability to retain the absorbed liquid when subjected to mechanical loads as would be applied by the wearer in use. When subjected to such loading, liquid can leak from the second absorbent layer and rewet the layers above through which liquid was originally passed to the second absorbent layer. As the first absorbent layer and the cover layer are made from materials with little absorption capacity, the liquid expelled from the second absorbent layer will tend to reside next to the body surface of the wearer resulting in discomfort and possible staining of the wearers garments.

There is therefore a need for a thin sanitary absorbent article with an improved ability to retain liquids under load.

According to the present invention there is provided a sanitary napkin adapted to be worn in the crotch portion of an undergarment comprising a fibrous fluid permeable, body facing cover layer and an absorbent system adjacent said cover layer for receiving liquid therefrom, said napkin having a thickness of less than or equal to 5 mm, a capacity of at least 18 grams, a rewet potential of less than or equal to 0.8 grams, and a flexural resistance of less than 700 grams.

The "rewet potential" as used herein is a measure of the ability of the absorbent article to retain liquid when subjected to mechanical pressure and is defined and determined according to the procedure described in detail below. The "thickness", the "capacity" and the "flexural resistance" of an absorbent article as used herein are also defined and determined in accordance with the test procedures described in detail below.

The inventors have found that a thin sanitary absorbent article can be made having surprisingly good rewet characteristics relative to its absorption capacity.

Preferably, the sanitary napkin has a rewet potential of less than 0.8 grams and more preferably a re-wet potential of less than 0.3 grams.

In a preferred embodiment, the absorbent system includes superabsorbent material, such as superabsorbent polymer. In one embodiment, the absorbent system comprises a blend of cellulosic fibers and superabsorbent material.

In a preferred embodiment, the absorbent system includes first absorbent layer underlying the cover layer for transferring liquid from the cover layer to a second absorbent layer. In a preferred embodiment, the first absorbent layer comprises a material having a structure with relatively open pores for efficiently absorbing liquid from the cover layer and transferring the liquid to the second absorbent layer. The first absorbent layer may comprise a material having a density in the range from about 0.04 to 0.05 g/cc, a basis weight of between about 80 to 110 g/m$^2$ and a thickness in the range of about 2 to 3 mm.

Advantageously, the absorbent system includes a second absorbent layer having a basis weight from about 100 g/m$^2$ to about 700 g/m$^2$ which has been air-laid as a bottom layer of pulp, a middle layer of pulp and superabsorbent polymer disposed in amongst the pulp, and a top layer containing at least some pulp. The second absorbent layer preferably has a density of more than about 0.25 g/cc and more preferably from about 0.3 to 0.4 g/cc.

Preferably, the second absorbent layer includes from about 5 weight percent to about 60 weight percent superabsorbent polymer, and more preferably in the range of about 30 to 40 weight percent superabsorbent polymer. The second absorbent layer preferably has a basis weight in the range from about 150 g/m$^2$ to about 350 g/m$^2$ and more preferably in the range from about 200 g/m$^2$ to about 300 g/m$^2$.

In a preferred embodiment, the napkin has at least one and preferably a plurality of spaced-apart elongate channel formations arranged to direct liquid therealong for subsequent absorption into the first absorbent layer. The channels may be formed in the cover layer and/or the first absorbent layer and/or between the two.

The channel(s) may extend obliquely of the longitudinal axis and may be linear or arcuate.

The inventors have found that the provision of channels has a significant affect in reducing the rewet potential. The channels serve to distribute liquid over the surface or near surface portion of the napkin away from the initial deposition site so that liquid is presented for absorption to the first absorbent layer over a large proportion of its surface area. This increases the effectiveness with which the second absorbent layer is able to draw and retain liquid from the first absorbent layer.

Advantageously, the channel(s) may be formed by applying pressure to localized regions of the napkin, for example by embossing, which has the simultaneous effect of densifying the material at the floor of the channel, making it less pervious to liquid and thereby enabling liquid to flow further along the channel before being absorbed.

In a preferred embodiment, the sanitary absorbent napkin comprises a barrier layer which is substantially adjacent the second absorbent layer and impervious to liquid absorbed by the second absorbent layer.

BRIEF DESCRIPTION OF THE DRAWINGS

Examples of embodiments of the present invention will now be described with reference to the drawings, in which.

DESCRIPTION OF THE PREFERRED EMBODIMENTS

Figure 1:
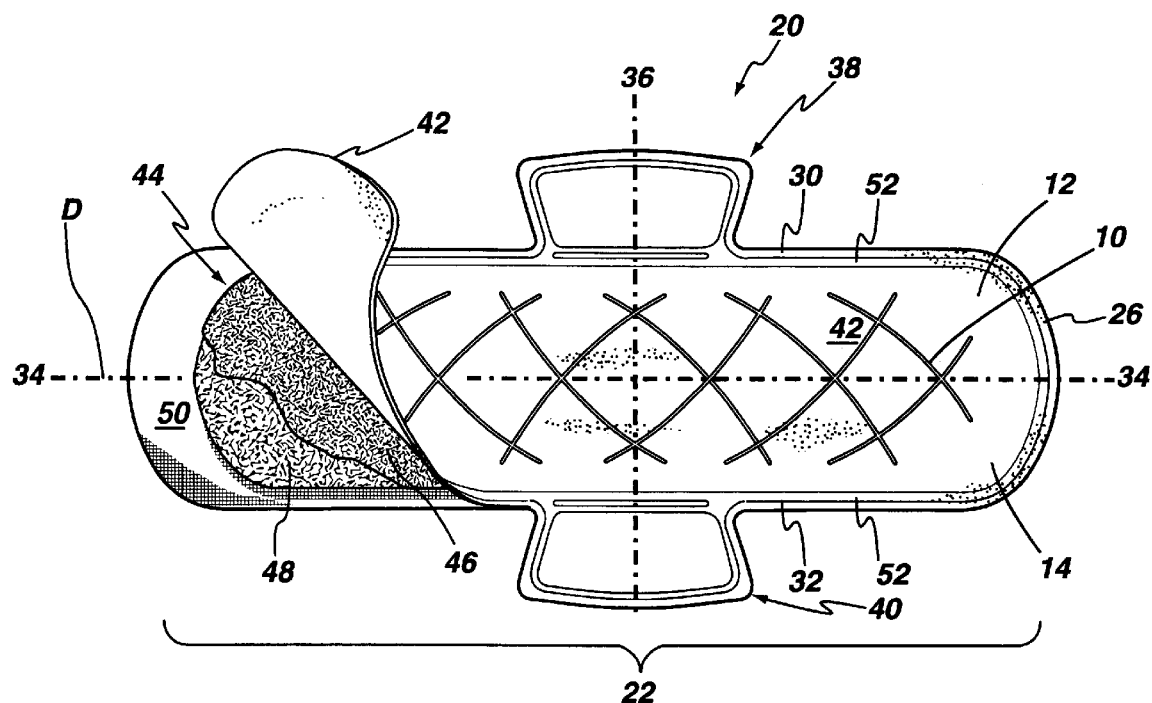
FIG. 1 is a top elevational view of a sanitary napkin in accordance with an embodiment of the present invention, the cover layer of the sanitary napkin being partly removed to show the absorbent system.
Figure 2:
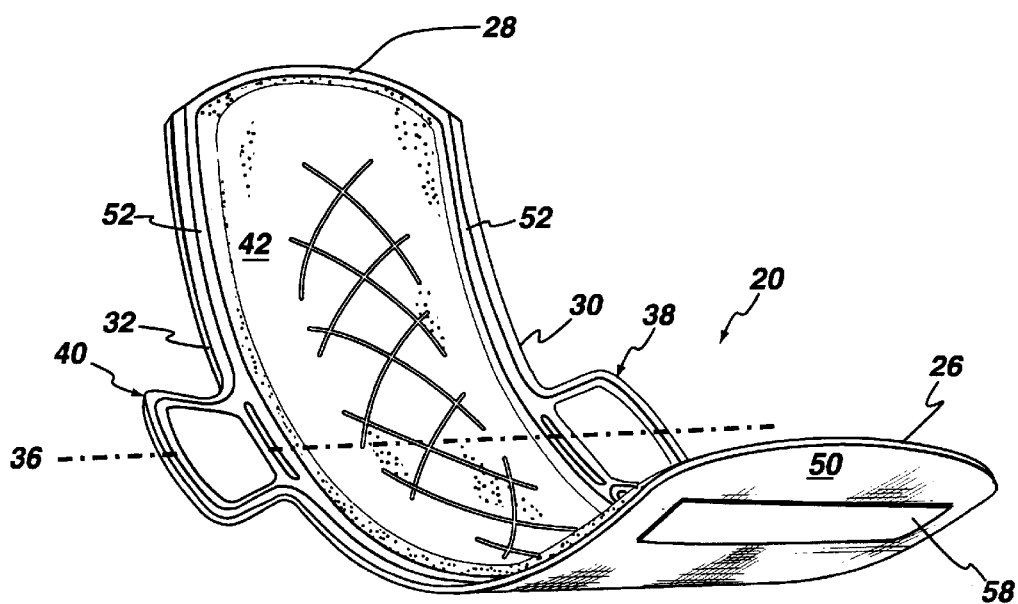
FIG. 2 is a perspective view of the sanitary napkin of FIG. 1, depicted in a position attained when the sanitary napkin is placed in the undergarment of a wearer.

Referring to FIGS. 1 and 2, there is shown an embodiment of the present invention, a feminine sanitary napkin 20.

The sanitary napkin 20 has a main body 22 with a first transverse side 26 defining a front portion thereof and a second transverse side 28 defining a rear portion thereof. The main body also has two longitudinal sides, namely a longitudinal side 30 and a longitudinal side 32. The sanitary napkin 20 has a thickness not exceeding about 5 mm. Preferably, the thickness is less than 3.5 mm, more preferably less than 3 mm, and most preferably it is less than 2 mm. A particularly preferred thickness is about 2.8 mm.

The sanitary napkin 20 has a longitudinal centerline 34 that is an imaginary line bisecting the sanitary napkin 20 in two identical halves.

In the embodiments shown in the drawings the sanitary napkin is provided with a pair of side flaps 38, 40. The flaps 38, 40 project laterally outward from each of the longitudinal sides 30, 32 and are adapted to be folded over a crotch portion of a wearer's undergarment. The flaps 38, 40 are in the shape of an isosceles trapezoid with the top adjoining the longitudinal side and the base at the distal end.

The main body 22 also has an imaginary transverse centerline 36 perpendicular to the longitudinal centerline 34 and simultaneously bisecting the flaps 38, 40.

Figure 4:
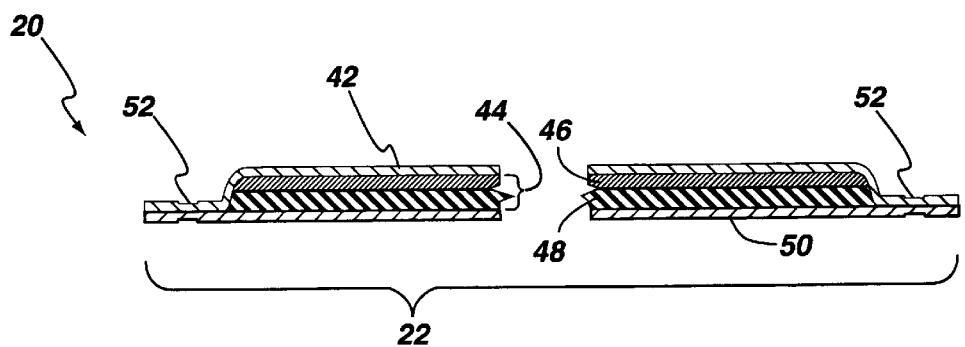
FIG. 4 is a cross-sectional view taken along the longitudinal centerline of the sanitary napkin shown in FIG. 3.

As depicted in FIG. 4, the main body 22 is of a laminate construction and preferably comprises a fibrous fluid-permeable body facing cover layer 42, an absorbent system 44, and a fluid-impervious barrier layer 50. The absorbent system has preferably two components, namely a first absorbent layer 46 (commonly known as "transfer layer") and a second absorbent layer 48 (commonly known as an "absorbent core"). Alternatively, a single layer, namely the second absorbent layer 48, can form the absorbent system 44. Each of these layers is described hereinbelow.

Main Body—Cover Layer

The cover layer 42 may be a relatively low density, bulky, high-loft non-woven web material. The cover layer 42 may be composed of only one type of fiber, such as polyester or polypropylene or it may be composed of bi-component or conjugate fibers having a low melting point component and a high melting point component. The fibers may be selected from a variety of natural and synthetic materials such as nylon, polyester, rayon (in combination with other fibers), cotton, acrylic fiber and the like and combinations thereof. An example is the non-woven cover layer of sanitary napkins sold by Johnson & Johnson Inc. of Montreal, Canada under the trademark Stayfree Ultra-Thin Cottony Dry Cover.

Bi-component fibers may be made up of a polyester layer and a polyethylene sheath. The use of appropriate bi-component materials results in a fusible non-woven fabric. Examples of such fusible fabrics are described in U.S. Pat. No. 4,555,446 issued Nov. 50, 1985 to Mays. Using a fusible fabric increases the ease with which the cover layer may be mounted to the adjacent first absorbent layer and/or to the barrier layer.

The cover layer 42 preferably has a relatively high degree of wettability, although the individual fibers comprising the cover may not be particularly hydrophilic. The cover material should also contain a great number of relatively large pores. This is because the cover layer 42 is intended to take-up body fluid rapidly and transport it away from the body and the point of deposition. Advantageously, the fibers which make up the cover layer 42 should not lose their physical properties when they are wetted, in other words they should not collapse or lose their resiliency when subjected to water or body fluid. The cover layer 42 may be treated to allow fluid to pass through it readily. The cover layer 42 also functions to transfer the fluid quickly to the other layers of the absorbent system 44. Thus, the cover layer 42 is advantageously wettable, and porous. When composed of synthetic hydrophobic fibers such as polypropylene or bi-component fibers, the cover layer 42 may be treated with a surfactant to impart the desired degree of wettability.

The cover layer 42 may be fused, e.g., by embossing to the remainder of the absorbent system 44 by fusing the cover to the underlying layer in order to assist fluid transport from the cover to the absorbent system. Such fusion may be effected locally, at a plurality of sites or over the entire contact surface of the cover layer 42 absorbent system 44. Alternatively, the cover layer 42 may be attached to the absorbent system 44 by other means such as by adhesive.

Main Body—Absorbent System—First Absorbent Layer

Adjacent to the cover layer 42 on its inner side and bonded to the cover layer 42 is a first absorbent layer 46 that forms part of the absorbent system 44. The first absorbent layer 46 provides the means of receiving body fluid from the cover layer 42 and holding it until an underlying second absorbent layer has an opportunity to absorb the fluid, and therefore acts as a fluid transfer or acquisition layer.

The first absorbent layer 46 is, preferably, more dense than and has a larger proportion of smaller pores than the cover layer 42. These attributes allow the first absorbent layer 46 to contain body fluid and hold it away from the outer side of the cover layer 42, thereby preventing the fluid from rewetting the cover layer 42 and its surface. However, the first absorbent layer 46 is, preferably, not so dense as to prevent the passage of the fluid through the layer 46 into the underlying second absorbent layer 48.

The first absorbent layer 46 may be composed of fibrous materials, such as wood pulp, polyester, rayon, flexible foam, or the like, or combinations thereof. The first absorbent layer 46 may also comprise thermoplastic fibers for the purpose of stabilizing the layer and maintaining its structural integrity. The first absorbent layer 46 may be treated with surfactant on one or both sides in order to increase its wettability, although generally the first absorbent layer 46 is relatively hydrophilic and may not require treatment. The first absorbent layer 46 is preferably bonded or adhered on both sides to the adjacent layers, i.e. the cover layer 42 and an underlying second absorbent layer 48.

Materials particularly suitable for use in the first absorbent layer 46, which the inventors have found contribute to reducing the rewet potential have a density in the range of about 0.04 to 0.05 g/cc, a basis weight in the range from about 80 to 110 g/m$^2$ and a thickness in the range of about 2 to 3 mm and in particular a thickness of 2.6 mm. Examples of suitable materials for the first absorbent layer are through air bonded pulp sold by Buckeye of Memphis, Tenn., under the designation VIZORB 3008, which has a basis weight of 110 g/m$^2$ and VIZORB 3010, which has a basis weight of 90 g/m$^2$.

Main Body—Absorbent System—Second Absorbent Layer

Immediately adjacent to and bonded to the first absorbent layer 46 is the second absorbent layer 48.

In one embodiment, the second absorbent layer 48 is a blend or mixture of cellulosic fibers and superabsorbent disposed in and amongst fibers of that pulp.

In a specific example, the second absorbent layer 48 is a material containing from about 40 weight percent to about 95 weight percent cellulosic fibers; and from about 5 weight percent to about 60 weight percent SAP (superabsorbent polymers). The material has a water content of less than about 10 weight percent. As used herein, the phrase "weight percent" means weight of substance per weight of final material. By way of example, 10 weight percent SAP means 10 g/m$^2$ SAP per 100 g/m$^2$ basis weight of the material.

Cellulosic fibers that can be used in the second absorbent layer 48 are well known in the art and include wood pulp, cotton, flax and peat moss. Wood pulp is preferred. Pulps can be obtained from mechanical or chemi-mechanical, sulfite, kraft, pulping reject materials, organic solvent pulps, etc. Both softwood and hardwood species are useful. Softwood pulps are preferred. It is not necessary to treat cellulosic fibers with chemical debonding agents, cross-linking agents and the like for use in the present material.

The second absorbent layer 48 can contain any superabsorbent polymer (SAP), which SAPs are well known in the art. For the purposes of the present invention, the term "superabsorbent polymer" (or "SAP") refers to materials which are capable of absorbing and retaining at least about 10 times their weight in body fluids under a 0.5 psi pressure. The superabsorbent polymer particles of the invention may be inorganic or organic crosslinked hydrophilic polymers, such as polyvinyl alcohols, polyethylene oxides, crosslinked starches, guar gum, xanthan gum, and the like. The particles may be in the form of a powder, grains, granules, or fibers. Preferred superabsorbent polymer particles for use in the present invention are crosslinked polyacrylates, such as the product offered by Sumitomo Seika Chemicals Co., Ltd. Of Osaka, Japan, under the designation of SA60N Type II*, and the product offered by Chemical International, Inc. of Palatine, Ill., under the designation of 2100A*.

In a specific example the second absorbent layer 48 is a material containing from about 40 to about 95 weight percent cellulosic fibers and, more specifically from about 60 to about 80 weight percent cellulosic fibers. Such a material may contain from about 5 to about 60 weight percent SAP, preferably from about 20 to about 55 weight percent SAP, even more preferably from about 30 to about 45 weight percent SAP, and most preferably about 40 weight percent SAP.

In a preferred embodiment, the second absorbent layer 48 is manufactured by using air-laying means. In accordance with FIG. 5, cellulosic fibers (e.g., pulp) are processed using a hammer mill to individualize the fibers. The individualized fibers are blended with SAP granules in a blending system 1 and pneumatically conveyed into a series of forming heads 2. The blending and distribution of fibers and SAP granules can be controlled separately for each forming head. Controlled air circulation and winged agitators in each chamber produce uniform mixture and distribution of pulp and SAP. The SAP can be thoroughly and homogeneously blended throughout the material or contained only in specific strata by distributing it to selected forming heads. Fibers (and SAP) from each forming chamber are deposited by vacuum onto a forming wire 3 thus forming a layered absorbent web. The web is subsequently compressed using calendars 4 to achieve desirable density. The densified web is wound into a roll 5 using conventional winding equipment. The forming wire 3 can be covered with tissue paper to reduce the loss of material. The tissue paper layer can be removed prior to calendering or incorporated into the formed material. In a possible variant, the first absorbent layer 46 can be formed integrally with the second absorbent layer 48 to provide a unitized absorbent system 44. This can be achieved by providing the apparatus depicted in FIG. 5 with an additional forming head (not shown in the drawings) to deposit on the second absorbent layer 48, by air laying and prior to calendering, a layer of material to form the first absorbent layer 46.

The second absorbent layer 48 of the present invention is of high density and in a specific example has a density of greater than about 0.25 g/cc. Specifically, the second absorbent layer 48 may have a density in the range of from about 0.30 g/cc to about 0.50 g/cc. More specifically, the density is from about 0.30 g/cc to about 0.45 g/cc and, even more specifically from about 0.30 g/cc to about 0.40 g/cc.

Figure 5:
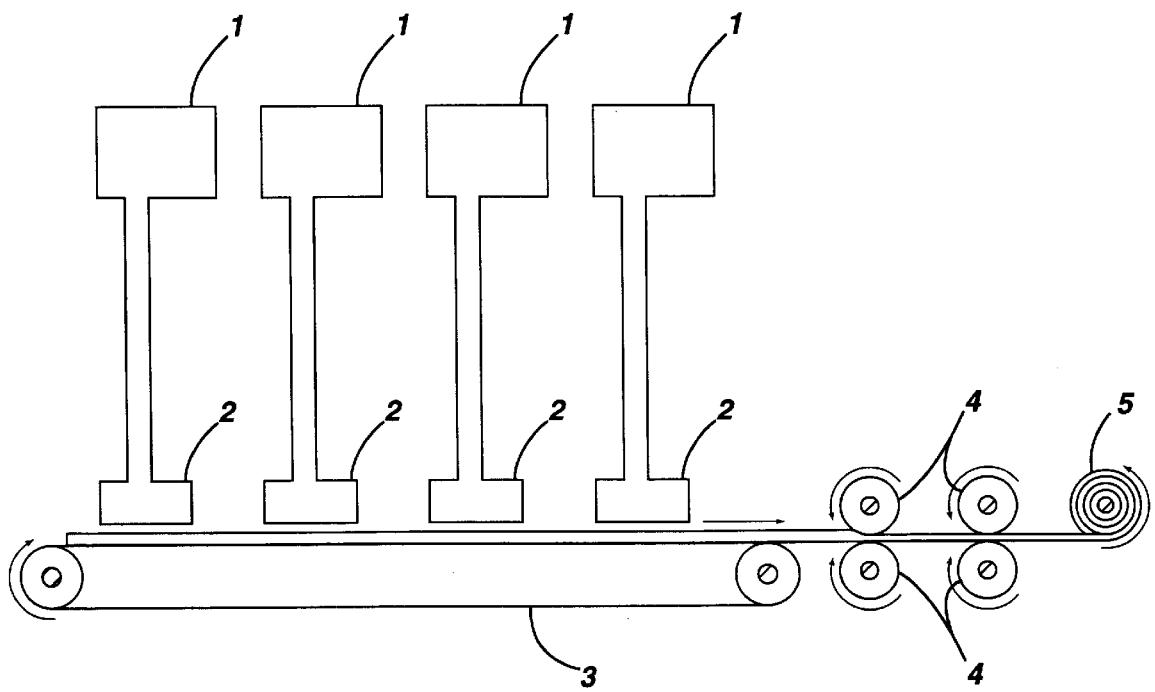
FIG. 5 is a schematic illustration of means for air-laying absorbent material for making an example of an second absorbent layer of the sanitary napkin according to an embodiment of the present invention, using four air-laying heads followed by means for compacting the air-layered material.

Air-laid absorbents are typically produced with a low density. To achieve higher density levels, such as the examples of the second absorbent layer 48 given above, the air-laid material is compacted using calenders as shown in FIG. 5. Compaction is accomplished using means well known in the art. Typically such compaction is carried out at a temperature of about 100 degrees C. and a load of about 130 Newtons per millimeter. The upper compaction roll is typically made of steel while the lower compaction roll is a flexroll having a hardness of about 85 SH D. It is preferred that both the upper and lower compaction rolls be smooth, although the upper roll can be engraved.

In one embodiment the second absorbent layer 48 has a ratio of Gurley stiffness, measured in milligrams (mg) to density, measured in grams per cubic centimeter (g/cc), of less than about 3700. In a specific example, that ratio of Gurley stiffness to density is less than about 3200 and, more specifically, less than about 3000.

Gurley stiffness is one of many indices of softness. Gurley stiffness measures the bendability or flexibility of absorbent materials. The lower the Gurley stiffness value, the more flexible the material. The Gurley stiffness values are measured using a Gurley Stiffness Tester (Model No. 4171 E), manufactured by Gurley Precision Instruments of Troy, N.Y. The instrument measures the externally applied moment required to produce a given deflection of a test strip of specific dimensions fixed at one end and having a concentrated load applied to the other end. The results are obtained in "Gurley Stiffness" values in units of milligrams.

The second absorbent layer 48 is strong in light of its softness. Pad integrity is a well-known measurement of absorbent material strength. In a specific embodiment the second absorbent layer 48 demonstrates strength (high pad integrity) over a wide range of densities. In a specific example the second absorbent layer 48 has a pad integrity, measured in Newtons (N), to density (g/cc) ratio of greater than about 25.0. In a more specific example, that ratio is greater than about 30.0 and, could even be greater than about 35.0. The pad integrity is a test performed on an Instron Universal Testing Machine. Essentially, the test measures the load required to pierce through the test sample, as described in the PFI Method of 1981. A test sample having dimensions of 50 mm by 50 mm is clamped on the Instron with a suitable fastening device. A 20 mm diameter piston traveling at the rate of 50 mm/min punctures the stationary sample. The force required to puncture the sample is measured in Newtons (N).

The second absorbent layer 48 can be prepared over a wide range of basis weights. The second absorbent layer 48 can have a basis weight in the range of from about 100 g/m² to about 700 g/m². In a specific example, the basis weight ranges from about 150 g/m² to about 400 g/m². Preferably the basis weight ranges from about 200 g/m² to about 350 g/m² and, more preferably, to about 300 g/m².

The second absorbent layer 48 functions synergistically with the first absorbent layer to reduce the rewet potential. The first absorbent layer having a relatively open pore structure readily absorbs and disperses liquid laterally within its bulk and readily transfers the liquid to the receiving surface of the second absorbent layer. In turn, the second absorbent layer having good capillarity efficiently draws liquid into its bulk from the first absorbent layer. Once the liquid has been absorbed into superabsorbent polymer, the liquid cannot be subsequently released by applying pressure. Therefore, the liquid absorbed into the superabsorbent material becomes permanently entrapped. At the same time, the strength with which second absorbent layer intakes liquid from the first absorbent layer helps to reduce the proportion of liquid held in the first absorbent layer, thereby reducing the amount of liquid that returns to the cover layer when the napkin is subjected to mechanical loading. Furthermore, the first absorbent layer has a relatively high capillarity so that any concentration of liquid in the first absorbent layer resulting from mechanical loading can be redistributed within the material to lower concentrations, again reducing the amount of liquid which can return to the cover layer.

In a specific embodiment, the second absorbent layer contains in the range from about 30 to 40 weight percent superabsorbent material, has a basis weight in the range from about 200 to 400 g/m² and a density in the range from about 0.2 to 0.45 g/cc.

The second absorbent layer 48 can be formed as three or four lamina or strata. Those strata include a bottom layer, one or two middle layers and a top layer. Specific examples of three and four layer material are set forth below. The SAP can be included in any or all of the layers. The concentration (weight percent) of SAP in each layer can vary as can the nature of the particular SAP.

An interesting characteristic of the second absorbent layer 48 is its ability to retain SAP when subjected to mechanical stress. The second absorbent layer 48 retained over 85 percent by weight of its SAP content when subjected to 10 minutes of rigorous shaking. Specifically, a material of this invention retains over 90 percent, more specifically over 95 percent and, even more specifically over 99 percent of its SAP under these mechanical stresses. The percent of SAP retained was determined by shaking the material in a Ro-Tap Sieve Shaker manufactured by W. S. Tyler Co., Cleveland Ohio. More specifically the sample is placed in a 28-mesh (Tyler series) sieve. Additional sieves of 35-mesh and 150-mesh were attached to the first sieve forming a column of increasingly fine sieves. The column of sieves was capped on either end to prevent the loss of fiber and/or SAP. The sieve column was placed in the shaker and agitated for 10 minutes. The amount of SAP granules shaken loose from the sample, "free SAP", was determined by combining the residue contained in each of the sieves and separating the cellulosic fiber from the SAP.

Even where prepared as from multiple layers, the final thickness of the formed second absorbent layer 48 is low. The thickness can vary from about 0.5 mm to about 2.5 mm. In a specific example, the thickness is from about 1.0 mm to about 2.0 mm and, even more specifically from about 1.25 mm to about 1.75 mm.

Figure 6A:
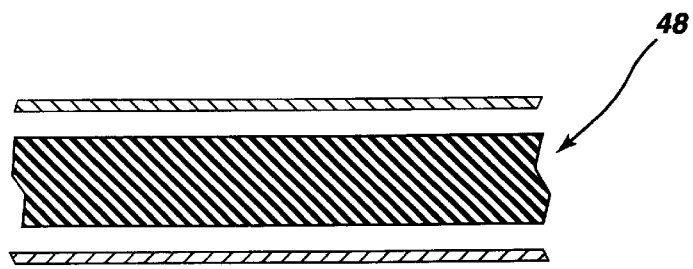
FIG. 6 shows three and four layer embodiments of an second absorbent layer that can be used in the sanitary napkin of an embodiment of invention.
Figure 6B:
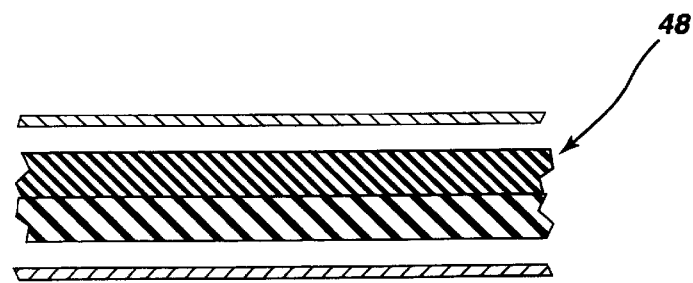

One embodiment of the second absorbent layer 48 particularly well suited for use in the sanitary napkin 20 is depicted in FIG. 6. Such second absorbent layer 48 has a basis weight of from about 200 g/m² to about 350 g/m² and a density between about 0.3 g/cc and 0.5 g/cc. In a specific example, the density is from about 0.3 g/cc to about 0.45 g/cc and, more specifically about 0.4 g/cc.

The second absorbent layer 48 depicted in FIG. 6 is air-laid as three strata: a bottom layer of pulp (without superabsorbent) with a basis weight of about 25 g/m²; a middle layer with a basis weight of about 150 g/m² and which contains from about 10 to about 30 g/m² superabsorbent and from about 120 g/m² to about 140 g m² pulp; and a top layer of pulp (without superabsorbent) with a basis weight of about 25 g/m². Relative to the total basis weight of the second absorbent layer 48, the level of superabsorbent ranges from about 5 to about 15 weight percent (g/m² of superabsorbent per g/m² material). In a specific example, the level of superabsorbent is from about 7.5 weight percent to about 12.5 weight percent of the material. More specifically, the material contains about 10 weight percent of superabsorbent. Thus, the middle layer of the material could contain from about 15 g/m² to about 25 g/m² superabsorbent and from about 125 g/m² to about 135 g/m² pulp and, more specifically about 20 g/m² superabsorbent and about 130 g/m² pulp. The middle layer containing pulp and superabsorbent can be laid down as a homogeneous blend or as a heterogeneous blend wherein the level of superabsorbent varies with proximity to the bottom layer.

In another embodiment, the second absorbent layer 48 is air-laid as four strata. In this embodiment, the middle layer referred to above is replaced with two middle layers: a first middle layer adjacent the top layer and a second middle layer adjacent the bottom layer. Each of the first and second middle layers independently comprises from about 10 to about 30 g/m² superabsorbent and from about 40 g m²to about 65 g/ m² pulp. When it is desired to keep absorbed fluid away from the cover layer 42 the amount of superabsorbent in the first and second middle layers is adjusted such that there is a higher level of superabsorbent in the second middle layer. The superabsorbent in the first and second middle layers can be the same or a different superabsorbent.

In one embodiment, the cellulosic fiber for use in the second absorbent layer 48 is wood pulp. There are certain characteristics of wood pulp that make it particularly suitable for use. Cellulose in most wood pulps has a crystalline form known as Cellulose I which can be converted to a form known as Cellulose II. In the second absorbent layer 48, wood pulp with a substantial portion of the cellulose as Cellulose II could be used. Similarly, pulps having an increased fiber curl value are advantageous. Finally, pulps having reduced levels of hemicellulose are preferred. Means for treating pulps so as to optimize these characteristics are well known in the art. By way of example, treating wood pulp with liquid ammonia is known to convert cellulose to the Cellulose II structure and to increase the fiber curl value. Flash drying is known to increase the fiber curl value of pulp. Cold caustic treatment of pulp decreases hemicellulose content, increases fiber curl and converts cellulose to the Cellulose II form. Thus it could be advantageous that the cellulosic fibers used to produce the material of this invention contain at least a portion of cold caustic treated pulp.

A description of the cold caustic extraction process can be found in U.S. patent application Ser. No. 08/370,571, filed on Jan. 18, 1995, pending which application is a continuation-in-part application of U.S. patent application Ser. No. 08/184,377, now abandoned filed on Jan. 21, 1994. The disclosures of both of these applications are incorporated in their entirety herein by reference.

Briefly, a caustic treatment is typically carried out at a temperature less than about 60 degree C., but preferably at a temperature less than 50 degree C., and more preferably at a temperature between about 10 degree C. to 40 degree C. A preferred alkali metal salt solution is a sodium hydroxide solution newly made up or as a solution by-product in a pulp or paper mill operation, e.g., hemicaustic white liquor, oxidized white liquor and the like. Other alkali metal salts such as ammonium hydroxide and potassium hydroxide and the like can be employed. However, from a cost standpoint, the preferable salt is sodium hydroxide. The concentration of alkali metal salts is typically in a range from about 2 to about 25 weight percent of the solution, and preferably from about 6 to about 18 weight percent. Pulps for high rate, fast absorbing applications are preferably treated with alkali metal salt concentrations from about 10 to about 18 weight percent.

For further details on the structure and the method of construction of the second absorbent layer 48 the reader is invited to refer to the U.S. Pat. No. 5,866,242 granted on Feb. 2, 1999 to Tan et al. The contents of this document are hereby incorporated by reference.

Main Body—Barrier Layer

Underlying the absorbent system 44 is a barrier layer 50 comprising liquid-impervious material so as to prevent liquid that is entrapped in the absorbent system 44 from egressing the sanitary napkin and staining the wearer's undergarment. The barrier layer 50 is preferably made of polymeric film, although it may be made of liquid-impervious air-permeable material such as repellent-treated, non-woven or microporous films or foams.

The cover layer 42 and the barrier layer 50 are joined along their marginal portions so as to form an enclosure or flange seal that maintains the absorbent system 44 captive. The joint may be made by means of adhesives, heat-bonding, ultrasonic bonding, radio frequency sealing, mechanical crimping, and the like and combinations thereof. The peripheral seal line is shown in FIG. 1 by the reference numeral 52.

Flaps

The flaps 38 and 40 are preferably made as integral extensions of the cover layer 42 and the barrier layer 50. These integral extensions are joined to one another along their marginal seal portions by adhesives, heat-bonding, ultrasonic bonding, radio frequency sealing, mechanical crimping, and the like and combinations thereof. Most preferably, such joining is made at the same time the cover layer 42 and the barrier layer 50 are bonded to one another to enclose the absorbent system 44. Alternatively, the flaps may include absorbent material between the cover layer and the barrier layer extensions. Such absorbent material may be an extension of the first absorbent layer 46, the second absorbent layer 48 or both.

Adhesive System

Figure 3:
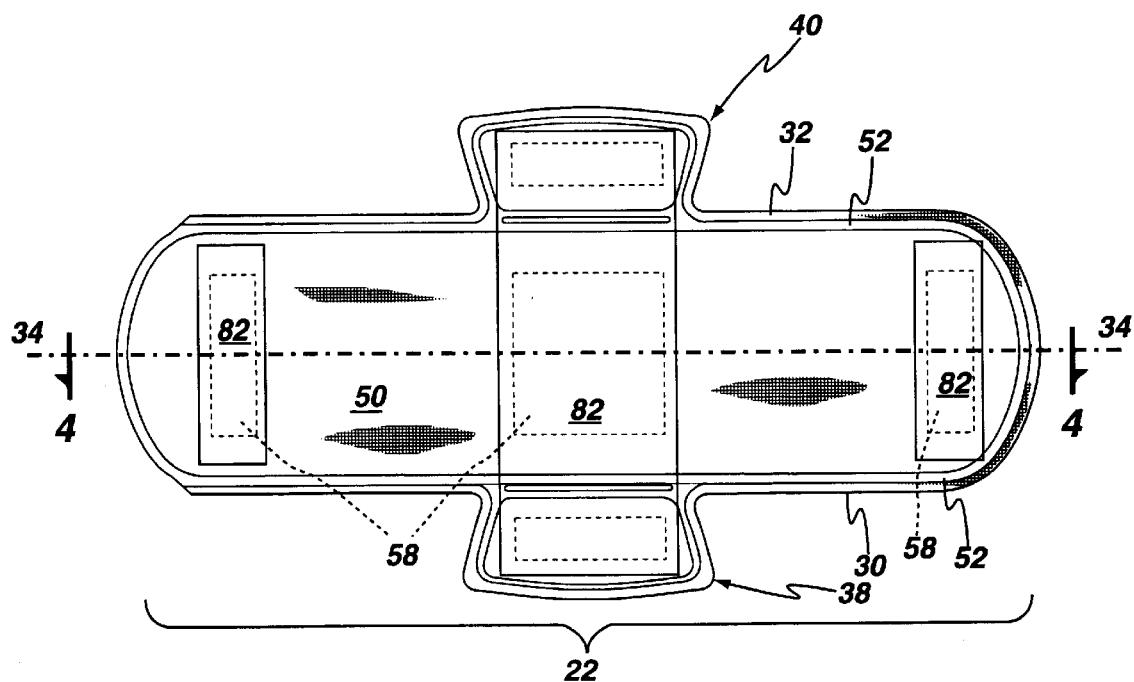
FIG. 3 is a bottom plan view of the sanitary napkin shown in FIG. 1.

Referring to FIGS. 2 and 3, in order to enhance the stability of the sanitary napkin, the garment facing surface of the barrier layer is provided with an undergarment attachment or positioning adhesive material 58, typically hot-melt adhesive material capable of establishing a temporary bond with the undergarment material. A suitable material is the composition designated HL-1491 XZP commercially available from H. B. Fuller Canada, Toronto, Ontario, Canada. The positioning adhesive 58 may be applied to the garment-facing surface of the barrier layer 50 in various patterns, including complete adhesive coverage, parallel longitudinal lines, a line of adhesive following the perimeter of the structure, transverse lines of adhesive or the like.

Standard release paper 82 (shown only in FIG. 3) covers the positioning adhesive 58 before the napkin is used to prevent the unwanted adherence of the napkin to itself or foreign objects. The release paper is of conventional construction (e.g. silicone coated wet-laid Kraft wood pulp) and suitable papers are available from Tekkote Corporation (Leonia, N.J., USA), and bear the designation FRASER 30#/61629.

Channel Formations

In a preferred embodiment, the sanitary napkin is provided with at least one and preferably more than one channel formation arranged to direct liquid along the channel (or channels) for subsequent absorption into the first absorbent layer. The inventors have found that the provision of channels contributes significantly in reducing the rewet potential. Preferably, the napkin has a plurality of elongate channels formed therein, which are spaced apart from each other and configured to channel liquid across the body-facing surface of the napkin, away from the region of initial deposition.

The provision of one or more channels adjacent the cover layer enables liquid to be transported rapidly over the napkin so that different regions of the first absorbent layer act effectively to absorb the liquid. This helps to ensure that liquid is presented to a larger portion of the surface area of the second absorbent layer to increase the effectiveness of the second absorbent layer in drawing liquid from the first absorbent layer.

The napkin may be provided with a single channel or multiple channels, for example running along or parallel to the longitudinal axis along the length of the napkin, obliquely of the longitudinal axis, for example from one side of the napkin to the other or substantially perpendicular to the longitudinal axis. The channel(s) may have any shape which may be selected according to the particular application, for example the channels may be linear, arcuate or have a serpentine configuration or a mixture of these as well as other shapes, including a spiral and zig-zag patterns.

In one embodiment, the napkin has a plurality of discrete channel formations which are spaced apart from and intersect one another. An example of such an embodiment is shown in FIG. 1. Referring to FIG. 1, the napkin 20 is provided with a plurality of arcuate channels 10 which extend generally obliquely of the longitudinal centre line 34 from one side portion 12 to the opposite side portion 14. This design efficiently conducts liquid simultaneously along the length and across the width of the napkin. The channel formation may be formed in the cover layer and/or in the first absorbent layer. The channels may be formed advantageously by applying localised pressure to the material as for example is used in embossing. The applied pressure results in densifying the material which defines the floor of the channel rendering it less pervious to liquid and so extending the distance over which the liquid can travel before absorption. The first absorbent layer is preferably relatively thick in comparison with the other layers of the napkin which enables relatively deep channels to be formed. Advantageously, portions of the first absorbent layer laterally adjacent to the channel remain relatively thick and retain their original, relatively open pore structure allowing liquid to be efficiently drawn from the channel. Advantageously, the first absorbent layer comprises thermoplastic fibres. The provision of thermoplastic fibres assists in the formation of a stable and permanent channel when the thermoplastic fibres and subjected to heat. When heat is applied, the thermoplastic fibres tend to fuse together to form a more rigid structure so that the original form of the channels is maintained during use and over time. Conveniently, the application of heat may be incorporated with the embossing process.

Method of Manufacture

The above-described embodiment of the sanitary napkin 20 is fabricated in a conventional manner in accordance with conventional techniques. Specifically, a laminate structure, sometimes referred to in the art as a web, is created. This laminate structure comprises an expanse of the materials from which the napkin will be created. In other words, the laminate structure comprises the following layers of material in a top-to-bottom order: an expanse of cover layer material; an expanse of first absorbent layer material; an expanse of second absorbent layer material (manufactured as described above); and finally an expanse of barrier layer. Some of the materials are necessarily not continuous within the laminate structure, and where such is the case, they are positioned precisely, one with respect to another, in the relationship they will occupy in the final products. The adjacent layers are bonded or adhered to one another. The cover layer material and the barrier layer material are then bonded together by applying pressure in the appropriate positions, and what will become the peripheral seal is created. (The seal may also be made by means of heat-bonding, ultrasonic bonding, radio frequency sealing, mechanical crimping, and the like and combinations thereof.) The sealed structure is then severed by conventional means (i.e. die-cutting, fluid-jet cutting, or by laser) from the web to create a discrete article.

As mentioned above, one or more channels may be formed adjacent the body facing surface of the napkin, and the channel(s) may be formed for example by embossing. The channel(s) may be formed by other techniques, including cutting, excavating, etching, molding and cauterizing, as well as other methods known to those skilled in the art. If embossing is used, the method may involve passing the sanitary napkin between a pair of rollers, in which one of the rollers includes projections configured to the desired embossing pattern. The projections compress and densify the material locally and may be applied to the cover layer, the absorbent system (particularly, the first absorbent layer) or a combination of the two. The degree of pressure applied during the embossing operation depending upon the type of material and its physical integrity. Finding the optimal process conditions in accordance with the specific application is within the scope of a person skilled in the art. In general, the embossing pressure should be selected to sufficiently densify the material locally to form the channels but not too high so as to sever the material. As mentioned above, the material may also be heated and this may be done conveniently by heating the embossing rollers. Ultrasonic embossing may also be used for forming the channel(s).

Advantageously, embossing helps to hold the various layers of the sanitary napkin together and reduces the likelihood of the cover layer or the barrier layer separating from the adjacent layers or coming loose when the sanitary napkin is bent. Preferably, the napkin is embossed at regular intervals over the majority and preferably the entirety of the its surface.

The positioning adhesive material is then applied to the barrier layer in the appropriate positions, and release paper is applied to cover the positioning adhesive. Alternatively, the positioning adhesive, or the positioning adhesive and the release paper may be applied to the web before the individual articles are severed therefrom.

Procedure for Measuring the Thickness of a Sanitary Article

As indicated earlier, the sanitary napkin 20 has a thickness of about 5 mm or less. The apparatus required to measure the thickness of the sanitary napkin is a footed dial (thickness) gauge with stand, available from Ames, with a 2" diameter foot at a pressure of 0.07 psig and a readout accurate to 0.001". A digital type apparatus is preferred. If the sanitary napkin sample is individually folded and wrapped, the sample is unwrapped and carefully flattened by hand. The release paper is removed from the sample and it is repositioned back gently across the positioning adhesive lines so as not to compress the sample, ensuring that the release paper lies flat across the sample. Flaps (if any) are not considered when taking the thickness reading in the center of the sample.

The foot of the gauge is raised and the sample is placed on the anvil such that the foot of the gauge is approximately centered the sample (or in the location of interest on the sample of interest). When lowering the foot, care must be taken to prevent the foot dropping onto the sample or undue force being applied. A load of 0.07 p.s.i.g. is applied to the sample and the read out is allowed to stabilize for approximately 5 seconds. The thickness reading is then taken. The thickness of the release paper covering the positioning adhesive is deducted from the total thickness.

Procedure for Measuring the Capacity of a Sanitary Article

The capacity of a sanitary napkin or other absorbent article is determined as follows. The napkin is prepared by removing any positioning adhesive release paper and conditioning the napkin at a temperature of 21°+/−1° C. and 50% +/−2% relative humidity for a period of two hours. The conditioned napkin is weighed to the nearest 0.1 gram and is then completely submerged, without being bent, twisted or folded, in a bath of 1% aqueous saline solution for 10 minutes. The napkin is then removed from the bath and suspended in a vertical position for 2 minutes to allow the saline solution to drain from the napkin. The napkin is then placed body-facing surface down onto an absorbent blotter, such as ED631-25 or equivalent, supplied by Ahistrom, Mount Holly Springs, Pa. 17065 U.S.A. A load which applies a uniform 17.6 grams per square centimeter is placed over the napkin to squeeze out excess fluid. The load may provided by a Plexiglass plate of 25 cm (10 inches) by 7 cm (2.75 inches) by 1.5 cm (0.25 inches) and weighing 350 grams above which are placed two weights each having dimensions of 13.4 cm (5.27 inches) by 3.6 cm (2.48 inches) by 2.2 cm (0.87 inches) and having a combined weight of 3 kg. The absorbent blotter is replaced every 30 seconds until the amount of fluid transferred to the absorbent blotter is less than 0.5 grams in a 30 second period. The napkin is weighed to the nearest 0.1 gram and the previously determined dry weight of the napkin is subtracted from this value. The difference in weight, expressed in grams defines the capacity of the napkin.

Procedure for Measuring Rewet Potential

The rewet potential is a measure of the ability of a napkin or other article to hold liquid within its structure when the napkin contains a relatively large quantity of liquid and is subjected to external mechanical pressure. The rewet potential is determined and defined by the following procedure.

Figure 7:
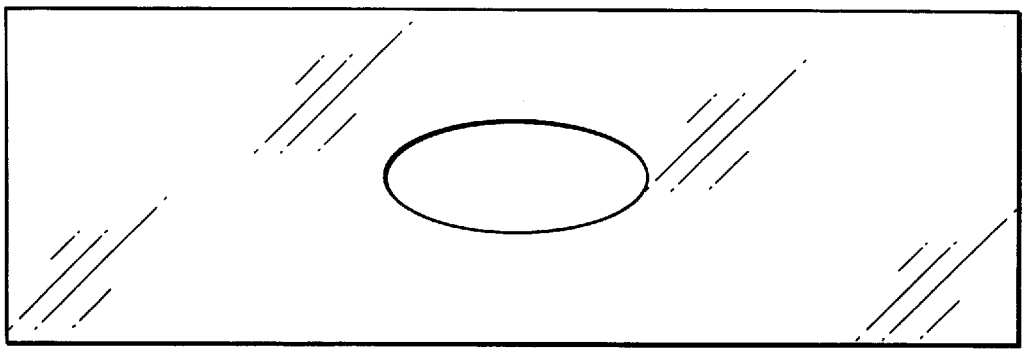
FIG. 7 shows a top view of a plate used in measuring the rewet potential.

The apparatus required for the test includes a stop watch with an accuracy to 1 sec and at least 5 minutes duration, a graduated glass cylinder of 10 ml capacity and having an internal diameter of approximately 12 mm, a quantity of test fluid, and a fluid penetration test orifice plate, as shown in FIG. 7. The test fluid is a synthetic menstrual fluid having a viscosity of xxx as is commonly known and used in the art. Referring to FIG. 7, the test plate is rectangular and made from Lexan and is 25.4 cm (10.0 inches) long by 7.6 cm (3.0 inches) wide by 1.27 cm (0.5 inches) thick. A concentric, elliptical orifice is formed through the plate having a major axis of length 3.8 cm and being parallel to the length of the plate and a minor axis of width 1.9 cm and being parallel to the width of the plate.

Figure 8:
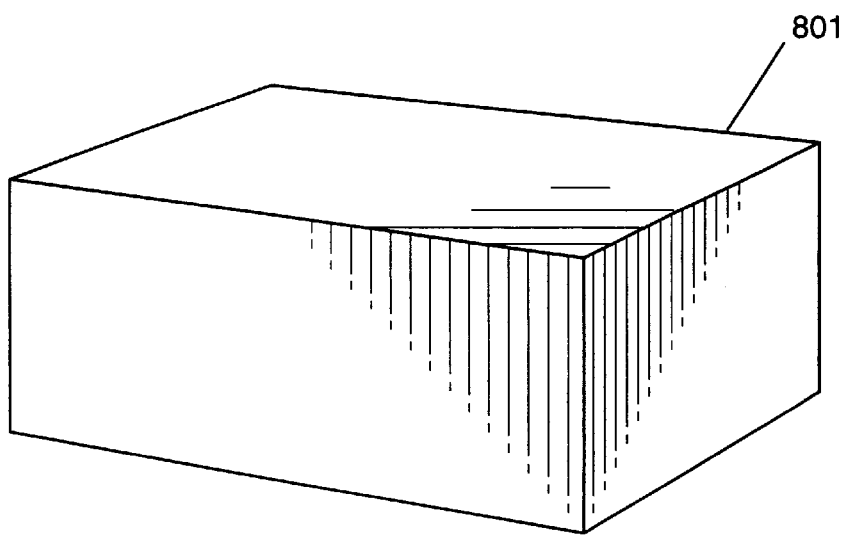
FIG. 8 shows a perspective view of a weight used in measuring the rewet potential.

The apparatus further includes a weighing machine or balance capable of weighing to an accuracy of ±0.001 g, a quantity of NuGauze general use sponges (10 cm×10 cm) (4 inches×4 inches)- 4 ply from Johnson & Johnson Medical Inc. Product Code 3634 (available from Johnson & Johnson Hospital Services, re: order number 7634), a standard weight of 2.22 kg (4.8 pounds) having dimensions 5.1 cm (2 inches) by 10.2 cm (4.0 inches) by approximately 5.4 cm (2.13 inches), as shown in FIG. 8, which applies a pressure of 4.14 kPa (0.6 psi) over the 5.1 by 10.2 cm (2 inches by 4 inches) surface.

Sample Preparation

The sanitary absorbent napkin or other absorbent article (with any packaging removed), the test fluid, the orifice plate and the graduated cylinders are conditioned at a temperature 21±1° C. and 50±2% relative humidity (RH) for a minimum of 2 hours prior to testing. If the napkin is folded, the creases are removed as far as possible by flattening and if the napkin is curved, the side gathers are cut through several times so that the sample can be flattened.

Procedure

Figure 9:
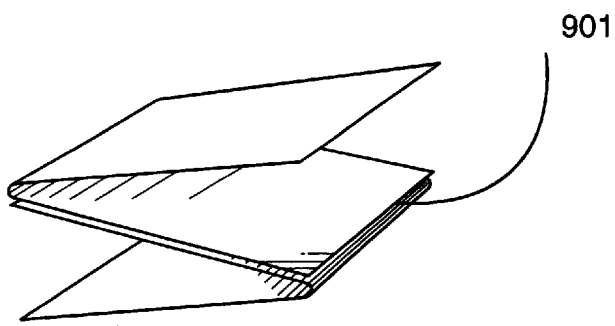
FIG. 9 shows a perspective view of a folded sponge for use in measuring the rewet potential.

Two sponges are folded with the creased edges placed opposing each other to create a layered structure of approximately 5 cm by 10 cm by 16 plies, as shown in FIG. 9. A 16 ply sponge 901 for each napkin sample to be tested is then weighed to the nearest 0.001 grams. The preconditioned sanitary napkin or other article is placed on a level surface, without removing the release paper and with the cover layer facing upwards.

The cleaned orifice plate is placed on the sample, with the orifice centered on the napkin's surface so that the major axis of the elliptical orifice is coincident with the longitudinal axis of the napkin. The orifice plate is placed such that the orifice is directly over or substantially adjacent to at least a portion of at least one channel. The graduated cylinder is then filled with 7 ml of test fluid.

Holding the spout of the graduated cylinder approximately 1 to 3 inches above the orifice plate, the test fluid is poured into the orifice such that the orifice is kept as full as possible without overflowing onto the face of the plate. As soon as the cover layer of the napkin first appears through the top surface of the fluid, the stop watch is started and an interval of 5 minutes is measured. After 5 minutes have elapsed, the orifice plate (shown in FIG. 7) is removed and the napkin is positioned on a hard level surface with the cover layer facing upwards. One pre-weighed 16 ply layered sponge is placed on and centered over the wetted area and the standard 2.22 kg weight (as shown in FIG. 8) is placed on top of the 16 ply layered sponge. Immediately after placing the sponge 901 and weight 801 on the napkin, the stop watch is started and after a 3 minute interval has elapsed the standard weight and 16 ply layered sponge are quickly removed. The wet weight of the 16 ply layered sponge is measured and recorded to the nearest 0.001 grams. The rewet value is then calculated as the difference in grams between the weight of the wet 16 ply layered sponge and the dry 16 ply layered sponge.

The measurement may be repeated for five replicates and, if necessary, the weight 801 is wiped clean before each run.

When conducting the above method, it is important that the tests are performed at a temperature of 21±1° C. and 65±2% relative humidity. It also important that the samples, all components of the apparatus and the test fluid are conditioned for a minimum of 8 hours at the condition specified above prior to testing. The sponges should not be weighed before they have been conditioned for a minimum of eight hours. The orifice plate should be thoroughly cleaned between test samples. Also, the test fluid container should not be left uncovered between testing of each sample as the evaporative effects will alter the fluids. If any of the above conditions are not met, the test results can be adversely affected. Also, the rewet value can be affected if the test fluid travels between the cover layer and the orifice plate.

Procedure for Measuring Flexural Resistance

The flexural resistance of the sanitary napkin is preferably in the range from about 400 g to about 800 g. The flexural resistance of a sanitary napkin is measured by peak bending stiffness. Peak bending stiffness is determined by a test that is modeled after the ASTM D 4032-82 CIRCULAR BEND PROCEDURE, the procedure being considerably modified and performed as follows. The CIRCULAR BEND PROCEDURE is a simultaneous multi-directional deformation of a material in which one face of a specimen becomes concave and the other face becomes convex. The CIRCULAR BEND PROCEDURE gives a force value related to flexural resistance, simultaneously averaging stiffness in all directions.

The apparatus necessary for the CIRCULAR BEND PROCEDURE is a modified Circular Bend Stiffness Tester, having the following parts:

1. A smooth-polished steel plate platform which is 102.0 mm by 102.0 by 6.35 mm having an 18.75 mm diameter orifice. The lap edge of the orifice should be at a 45 degree angle to a depth of 4.75 mm;
2. A plunger having an overall length of 72.2 mm, a diameter of 6.25 mm, a ball nose having a radius of 2.97 mm and a needle-point extending 0.88 mm therefrom having a 0.33 mm base diameter and a point having a radius of less than 0.5 mm, the plunger being mounted concentric with the orifice and having equal clearance on all sides. Note that the needle-point is merely to prevent lateral movement of the test specimen during testing. Therefore, if the needle-point significantly adversely affects the test specimen (for example, punctures an inflatable structure), than the needle-point should not be used. The bottom of the plunger should be set well above the top of the orifice plate. From this position, the downward stroke of the ball nose is to the exact bottom of the plate orifice;
3. A force-measurement gauge and more specifically an Instron inverted compression load cell. The load cell has a load range of from about 0.0 to about 2000.0 g;
4. An actuator and more specifically the Instron Model No. 1122 having an inverted compression load cell. The Instron 1122 is made by the Instron Engineering Corporation, Canton, Mass.

In order to perform the procedure for this test, as explained below, five representative sanitary napkins are necessary. From one of the five napkins to be tested, some number "Y" of 37.5 mm by 37.5 mm test specimens are cut. Specimens having portions in which a cover layer is joined directly to a barrier layer or which are a laminate of a cover layer, and a barrier layer without any component of the absorbent system, should not be tested. This test is more concerned with the overall flexibility of the sanitary napkin and not merely the peripheral portions thereof and, therefore, the flexibility of the present invention is more concerned with the flexibility of the absorbent portions of the sanitary napkin.

The test specimens should not be folded or bent by the test person, and the handling of specimens must be kept to a minimum and to the edges to avoid affecting flexural-resistance properties. From the four remaining sanitary napkins, an equal number "Y" of 37.5 mm by 37.5 mm specimens, identical to the specimens cut from the first napkin, are cut. Thus, the test person should have "Y" number of sets of five identical specimens.

The procedure for the CIRCULAR BEND PROCEDURE is as follows. The specimens are conditioned by leaving them in a room that is 21 degree Celsius plus or minus 1 degree Celsius and 50% plus or minus 2.0% relative humidity for a period of two hours. The test plate is leveled. The plunger speed is set at 50.0 cm per minute per full stroke length. A specimen is centered on the orifice platform below the plunger such that the cover layer 42 of the specimen is facing the plunger and the barrier layer 50 of the specimen is facing the platform. The indicator zero is checked and adjusted, if necessary. The plunger is actuated. Touching the specimen during the testing should be avoided. The maximum force reading to the nearest gram is recorded. The above steps are repeated until all five of the identical specimens have been tested.

Calculations

The peak bending stiffness for each specimen is the maximum force reading for that specimen. Remember that "Y" number of sets of five identical specimens were cut. Each set of five identical specimens is tested and the five values received for that set are averaged. Thus, the test person now has an average value for each of the "Y" sets tested. The flexural resistance for a sanitary napkin is the greatest of these average peak bending stiffnesses.

The sanitary napkin embodying the invention has surprisingly good rewet characteristics for a given absorption capacity and degree of flexibility providing a sanitary protection device which is thin, flexible and unobtrusive, offering a high level of comfort, and yet highly retentive, keeping liquid away from the wearer even when subjected to compressive stresses.

Applications of the product and methods of the present invention for sanitary and other health-care uses can be accomplished by any sanitary protection, incontinence, medical and absorbent methods and techniques as are presently or prospectively known to those skilled in the art. Thus, it is intended that the present application cover the modifications and variations of this invention provided that they come within the scope of the appended claims and their equivalents.

We claim:

1. A sanitary napkin adapted to be worn in a crotch portion of an undergarment comprising a fibrous fluid-permeable, body-facing cover layer and an absorbent system adjacent said cover layer for receiving liquid therefrom, said napkin having a thickness of about 5 mm or less, a capacity of at least 18 grams, a rewet potential of less than or equal to 0.8 grams as measured by the Procedure for Measuring Rewet Potential described herein and a flexural resistance of less than 700 grams.

2. A sanitary napkin as claimed in claim 1, wherein said rewet potential is less than about 0.5 g.

3. A sanitary napkin as claimed in claim 2, wherein said rewet potential is less than about 0.3 g.

4. A sanitary napkin as claimed in claim 1, wherein said absorbent system includes superabsorbent material.

5. A sanitary napkin as claimed in claim 4, wherein said absorbent system includes a blend of cellulosic fibers and superabsorbent material.

6. A sanitary napkin as claimed in claim 5, wherein said absorbent system comprises a first absorbent layer and a second absorbent layer, said second absorbent layer having a basis weight of from about 100 $g/m^2$ to about 700 $g/m^2$ which has been air-laid as a bottom layer of pulp, a middle layer of pulp intermixed with superabsorbent polymer, and a top layer containing at least some pulp.

7. A sanitary napkin as claimed in claim 6, wherein said second absorbent layer has a density of more than about 0.25 g/cc.

8. A sanitary napkin as claimed in claim 7, wherein said second absorbent layer has a density in the range from about 0.3 g/cc to about 0.5 g/cc.

9. A sanitary napkin as claimed in claim 8, wherein said second absorbent layer has a density in the range from about 0.3 g/cc to about 0.45 g/cc.

10. A sanitary absorbent napkin as claimed in claim 6, wherein the middle layer comprises a first middle layer adjacent the bottom layer and a second middle layer adjacent the top layer.

11. A sanitary napkin as claimed in claim 6, wherein said second absorbent layer includes from about 20 weight percent to about 55 weight percent suberabsorbent polymer.

12. A sanitary napkin as claimed in claim 11, wherein said second absorbent layer includes from about 30 weight percent to about 45 weight percent superabsorbent polymer.

13. A sanitary napkin as claimed in claim 12, wherein said second absorbent layer includes about 40 weight percent superabsorbent polymer.

14. A sanitary napkin as claimed in claim 6, wherein said second absorbent layer has a basis weight in the range from about 150 g/m² to about 350 g/m².

15. A sanitary napkin as claimed in claim 14, wherein said second absorbent layer has a basis weight in the range from about 200 g/m² to about 300 g/m².

16. A sanitary napkin as claimed in claim 15, wherein said second absorbent layer has a basis weight of about 250 g/m².

17. A sanitary napkin as claimed in claim 6, wherein said first absorbent layer is air laid over said second absorbent layer.

18. A sanitary napkin as claimed in claim 17, wherein said first absorbent layer comprises thermoplastic fibers.

19. A sanitary napkin as claimed in claim 17, wherein said first absorbent layer comprises a material having a density in the range from about 0.04 to 0.05 g/cc.

20. A sanitary napkin as claimed in claim 17, wherein said first absorbent layer comprises a material having a basis weight in the range from about 80 g/m² to about 110 g/m².

21. A sanitary napkin as claimed in claim 18, wherein said first absorbent layer has a thickness in the range from about 2 mm to about 3 mm.

22. A sanitary napkin as claimed in claim 6, wherein said second absorbent layer includes from about 5 weight percent to about 60 weight percent superabsorbent polymer.

23. A sanitary napkin as claimed in claim 22, having an elongate channel formation arranged to direct liquid there along for subsequent absorption into said absorbent system, wherein said elongate channel formation is formed by applying pressure to at least one of said cover layer and said absorbent system.

24. A sanitary napkin as claimed in claim 23, wherein said elongate channel formation is formed by applying heat to at least one of said cover layer and said absorbent system.

25. A sanitary napkin as claimed in claim 1, having an elongate channel formation arranged to direct liquid there along for subsequent absorption into said absorbent system.

26. A sanitary napkin as claimed in claim 25, wherein said elongate channel formation is arcuate in a plane parallel to said absorbent system.

27. A sanitary napkin as claimed in claim 25, wherein said elongate channel formation is formed in at least one of said cover and said absorbent system.

28. A sanitary napkin as claimed in claim 25, further comprising a plurality of said elongate channel formations spaced apart from each other.

29. A sanitary napkin as claimed in claim 28, wherein said elongate channel formations intersect each other.

30. A sanitary napkin as claimed in claim 25, wherein said channels comprise a floor and sides, the floor of said channel having a higher density than at least one side of said channel.

31. A sanitary napkin as claimed in claim 1, wherein, at the interface between said cover and said absorbent system, an elongate region is recessed in said absorbent system, said elongate region having a higher density than a second region adjacent thereto.

32. A sanitary napkin as claimed in claim 31, further comprising a plurality of said elongate regions.

33. A sanitary napkin as claimed in claim 1, further comprising a sheet of material disposed adjacent said second absorbent layer and away from said cover layer and being substantially impervious to liquid to be absorbed by said second absorbent layer.

34. A sanitary napkin as claimed in claim 1, wherein the thickness of the sanitary napkin is less than about 3 mm.

35. A sanitary napkin as claimed in claim 34, wherein the thickness of the sanitary napkin is about 2.8 mm.

36. A sanitary napkin as claimed in claim 1, further comprising a fastener for fastening said napkin to a garment of the wearer.

37. A sanitary napkin as claimed in claim 36, wherein said fastener comprises an adhesive fastener.

38. A sanitary napkin as claimed in claim 37, further comprising a flap carrying said adhesive fastener.

* * * * *